(12) United States Patent
Mehta

(10) Patent No.: US 9,749,716 B2
(45) Date of Patent: *Aug. 29, 2017

(54) TRANSMIT POWER SCALING METHOD AND SYSTEM TO DETECT OCCURRENCES USING GEOGRAPHICALLY DISTRIBUTED SENSORS

(71) Applicant: Indian Institute of Science (IISc), Bangalore (IN)

(72) Inventor: Neelesh B. Mehta, Bangalore (IN)

(73) Assignee: INDIAN INSTITUTE OF SCIENCE (IISC), Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/816,950

(22) Filed: Aug. 3, 2015

(65) Prior Publication Data

US 2015/0341439 A1 Nov. 26, 2015

Related U.S. Application Data

(63) Continuation of application No. 12/550,168, filed on Aug. 28, 2009, now Pat. No. 9,118,980.

(30) Foreign Application Priority Data

Feb. 17, 2009 (IN) .............................. 340/CHE/2009

(51) Int. Cl.
*H04L 29/08* (2006.01)
*H04W 52/48* (2009.01)
(Continued)

(52) U.S. Cl.
CPC ............... *H04Q 9/00* (2013.01); *H04L 67/12* (2013.01); *H04W 52/28* (2013.01); *G06F 19/3493* (2013.01); *H04Q 2209/20* (2013.01); *H04Q 2209/25* (2013.01); *H04Q 2209/40* (2013.01); *H04Q 2209/43* (2013.01); *H04W 4/005* (2013.01); *H04W 4/025* (2013.01); *H04W 52/0245* (2013.01); *H04W 84/005* (2013.01);
(Continued)

(58) Field of Classification Search
CPC ............. H04W 52/0245; H04W 4/005; H04W 84/005; H04W 4/025; H04L 67/12; G06F 19/3493; H04Q 2209/845; H04Q 2209/25
See application file for complete search history.

(56) References Cited

U.S. PATENT DOCUMENTS 6,980,106 B2 * 12/2005 Sutphin ................ G08B 25/012 340/539.22
7,065,465 B2 6/2006 Chen et al.
(Continued)

*Primary Examiner* — Sujoy Kundu
*Assistant Examiner* — L. Anderson
(74) *Attorney, Agent, or Firm* — Maschoff Brennan

(57) ABSTRACT

Sensors within sensor node networks may communicate bio-event or other types of measurement results/decisions between each other using signal transmission variations. Each sensor node within a network and between networks may transmit and receive signals. A sensor node may scale a signal transmission power in a manner that is proportional to a confidence level of a decision or measurement about an event being detected. Each sensor node will receive transmissions from neighboring nodes, and can refine an estimate about an occurrence of the event at its location based on received signal strengths, for example.

20 Claims, 8 Drawing Sheets

(51) Int. Cl.
*H04Q 9/00* (2006.01)
*H04W 52/28* (2009.01)
H04W 52/02 (2009.01)
H04W 4/02 (2009.01)
H04W 84/02 (2009.01)
H04W 4/00 (2009.01)
H04W 84/00 (2009.01)
G06F 19/00 (2011.01)
H04W 84/18 (2009.01)

(52) U.S. Cl.
CPC ............ *H04W 84/02* (2013.01); *H04W 84/18* (2013.01); *Y02B 60/50* (2013.01)

(56) References Cited

U.S. PATENT DOCUMENTS

| | | | |
|---|---|---|---|
| 7,429,923 B2* | 9/2008 | McKitterick | G06N 3/02 340/541 |
| 2007/0033153 A1 | 2/2007 | Yamanaka et al. | |
| 2010/0169021 A1* | 7/2010 | Moisio | G01V 1/008 702/15 |

* cited by examiner

TRANSMIT POWER SCALING METHOD AND SYSTEM TO DETECT OCCURRENCES USING GEOGRAPHICALLY DISTRIBUTED SENSORS

CROSS-REFERENCE TO RELATED APPLICATIONS

The present application is a continuation under 35 U.S.C. §120 of U.S. patent application Ser. No. 12/550,168, filed on Aug. 28, 2009 and now issued as U.S. Pat. No. 9,118,980, which claims priority under 35 U.S.C. §119(a) to a corresponding patent application filed in India and having application number 340/CHE/2009, filed on Feb. 17, 2009, the entire contents of each of which are herein incorporated by reference.

BACKGROUND

Public fears related to toxic or pollutant gases being radiated throughout an area have generated development of sensor networks that may provide real-time or near real-time early-warning signs for a wide array of chemical, biological and nuclear threats across the area. Sensor node networks may be deployed throughout cities and towns to measure, monitor, detect and notify the public of bio-events. Example bio-events that might be detected include presence of an intruder or multiple intruders, biological and chemical attacks, spread of infectious diseases, and an increase in pollen concentrations.

Sensors within sensor networks may include micro-electromechanical systems (MEMS) and other nanotechnology based biological and chemical sensors, which interact with one another to perform as peer-to-peer network elements with multilevel security and quality-of-service guarantees, spanning wireless, wired and satellite links, for example. The sensors may provide information to public authorities, which can then notify the public in a vicinity of a region where an infectious disease has been detected, for example. Given the geographically distributed nature of sensors in a sensor node network, a centralized architecture in which all information generated by the large number of sensors is collected by a central entity can become prohibitively expensive and impractical. The central entity would then also need to return a decision to all or some of the sensor nodes that instructs the sensor nodes to take additional action.

Each node in a sensor node network may detect an event by making periodic measurements of variables that help detect presence of the event, and then may make a decision about the presence or absence of the event. Dedicated communication links between pairs of nodes and between the nodes and a central unit are employed to enable the nodes to communicate their measurements and decisions amongst one another. Doing so helps each node to improve an accuracy of a decision. However, establishing communication protocols for use in communication between the sensors individually and for use in communication between the sensors and the central entity can become complicated making the sensor node network less appealing.

SUMMARY

The present application describes a computer-readable medium containing a set of instructions for causing a processing unit to perform the functions of receiving a measurement indicating a detected occurrence by a sensor, making a determination about a level of confidence that the occurrence relates to an event being monitored, and establishing a signal transmit power level of the sensor to be proportional to the level of confidence.

In another aspect, the present application describes a system for determining a transmit power level including a sensing unit, a transceiver and a processing unit. The sensing unit makes a measurement indicative of a detected occurrence. The transceiver receives and transmits wireless signals, and the processing unit receives the measurement and makes a determination about a level of confidence that the occurrence relates to an event being monitored. The processing unit also establishes a signal transmit power level of the transceiver to be proportional to the level of confidence.

In still another aspect, the present application describes a method for detecting occurrences using geographically distributed sensors. The method includes making measurements indicating detected occurrences by sensors, and each sensor making a determination about a level of confidence that an occurrence relates to an event being monitored. The method also includes each sensor broadcasting a signal with a power level proportional to the level of confidence determined by the sensor. The method further includes at each sensor, receiving signals broadcast by other sensors, and determining a signal strength of received signals. The method further includes each sensor adjusting the level of confidence that the occurrence relates to the event being monitored based on the signal strength of received signals, and each sensor rebroadcasting the signal with a power level proportional to the adjusted level of confidence determined by the sensor.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
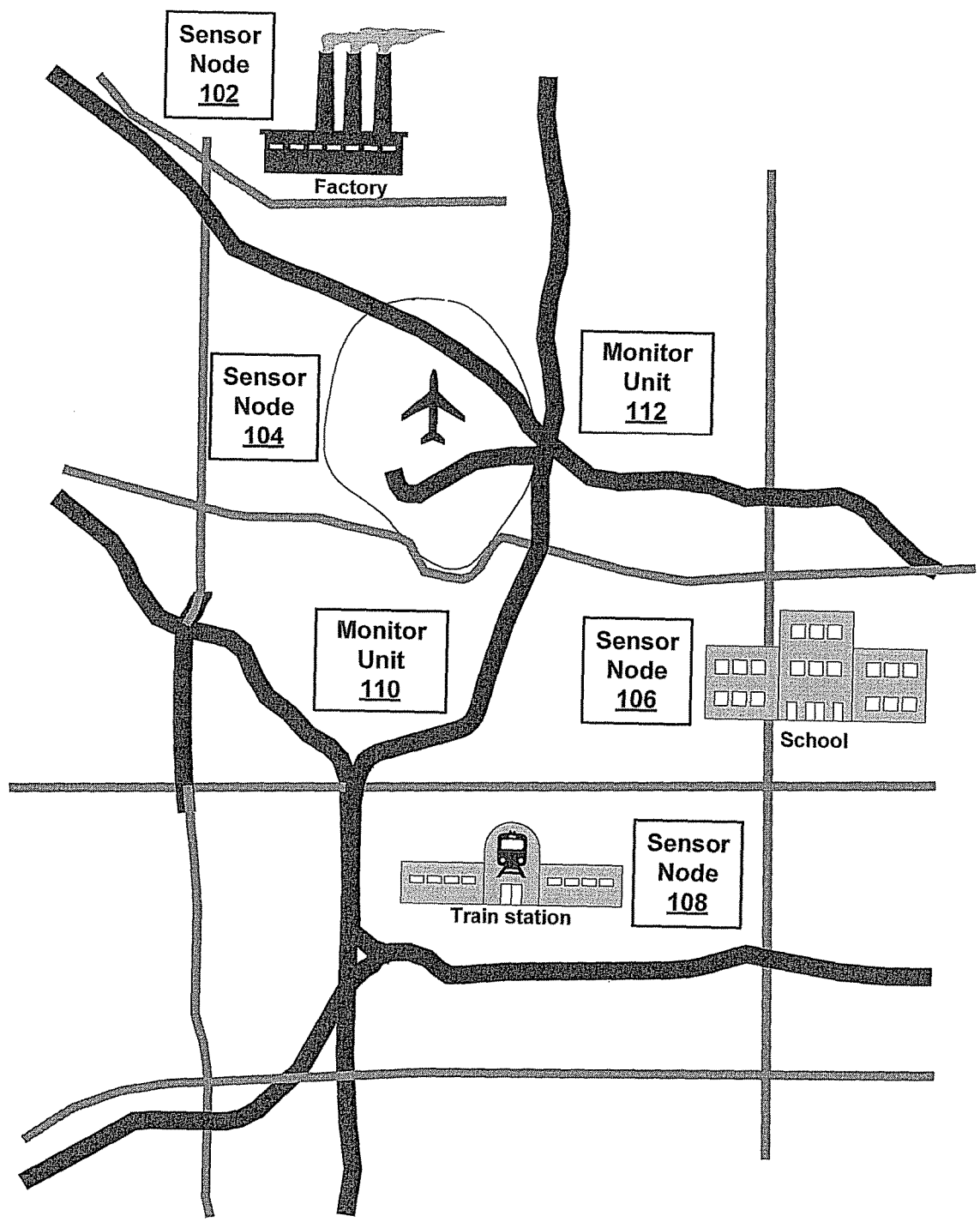
FIG. 1 illustrates an example conceptual geographical area and placement of example sensor nodes within the geographical area.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In the present application, sensors within sensor node networks may communicate bio-event or other types of measurement results/decisions between each other using signal transmission variations. Each sensor node within a network and between networks may transmit and receive signals. A sensor node may then scale a signal transmission power in a manner that is proportional to a confidence level of a decision or measurement about an event being detected. For example, a sensor node that is 90% confident that an event has been detected will transmit at a higher power than a sensor node that is only 40% confident. A confidence level can be derived through intermediate stages of signal processing algorithms used to perform a detection decision. In addition, a sensor node may also embed a message in a transmitted signal to convey more information, such as to expressly indicate the sensor node's confidence level of detection.

Each sensor node will receive transmissions from neighboring nodes if the neighboring nodes transmit at a sufficient transmission power. Based on received signal strength of transmissions, a sensor node may refine an estimate about an occurrence of the event at its location. For example, a sensor node that receives stronger signals than usual from neighbor sensor nodes may determine that it is more likely that the sensor node is also in the vicinity of the event. The sensor node may then update a confidence level of detection, and transmit signals at a high transmission power.

Using the methods described herein, no dedicated communication links between sensor nodes and/or between sensor node networks may be required. Also, sensor nodes that detect the event will automatically begin performing as beacons that warn about the occurrence of the event. Furthermore, since a sensor node that is more confident about detecting an event transmits at a higher power, a transmitted signal is received over a larger geographical area, which is desirable for many types of events that may be detected.

In addition, a transmit power level scaling method also enables a natural distributed manner of locally detecting a boundary of a detected event region, which may refer to a geographical area in which the event is detected by all sensor nodes within the area. A sensor node in an interior of the event region will receive stronger signals from many neighboring sensor nodes. On the other hand, a sensor node at the boundary of the event region will receive stronger signals from the sensor nodes within the event region, but weaker signals from sensor nodes outside the event region. A demarcation of a boundary region enables the boundary sensor nodes to notify the public to avoid the event region. For example, vehicles that receive the transmissions from the boundary nodes may reroute themselves to avoid the event region.

Referring now to the figures, FIG. 1 illustrates a conceptual geographical area and placement of example sensor nodes 102, 104, 106 and 108 within the geographical area. Within FIG. 1, the sensor nodes are positioned at various locations of interest, such as the sensor node 102 near a factory, the sensors node 104 near an airport, the sensor node 106 near a school, and the sensor node 108 near a train station. Of course, the sensor nodes may be positioned at any desired location, and at any distance relative to one another as will be described more fully below.

The sensor node 102, 104, 106 and 108 may include one or more sensors. Each sensor in the sensor node, or each sensor node 102, 104, 106 and 108 is capable of performing some processing, gathering sensory information and communicating with the other sensor nodes.

In addition, monitor units, such as monitor unit 110 and 112 may be positioned throughout the geographic area to receive signals from the sensor nodes 102, 104, 106 and 108. Alternatively, each sensor node may include a monitor unit. The monitor units 110 and 112 may generate warnings for the public based on received signals, or otherwise process received signals as described below.

Figure 2A:
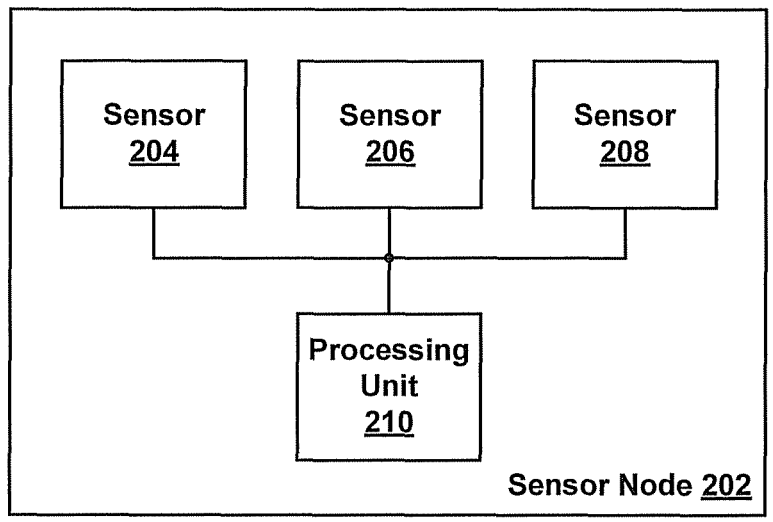
FIGS. 2A-2B are block diagrams illustrating examples of sensor nodes.

FIG. 2A is a block diagram illustrating one example of a sensor node 202. The sensor node 202 includes multiple sensors, such as sensor 204, 206 and 208 each connected to a processing unit 210. The sensor node 202 may alternatively only include one sensor.

Figure 2B:
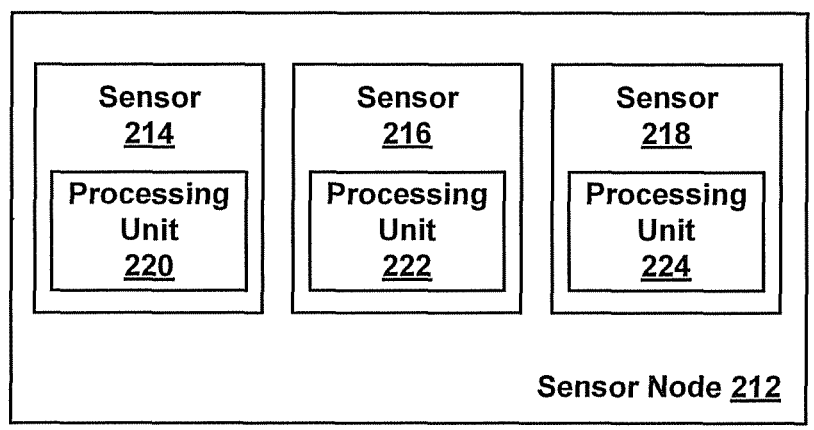

FIG. 2B is another block diagram illustrating another example of a sensor node 212. The sensor node 212 includes multiples sensors 214, 216 and 218 each of which includes a processing unit, such as processing units 220, 222 and 224.

FIGS. 2A and 2B illustrate two examples of sensor nodes, however, a sensor node may include many other configurations as well. Any number of sensors may be included, and connected to a central processing unit, or each sensor may include a processing unit. Additionally, sensors within a sensor node may be coupled via wire or wireless communication links, for example.

Figure 3:
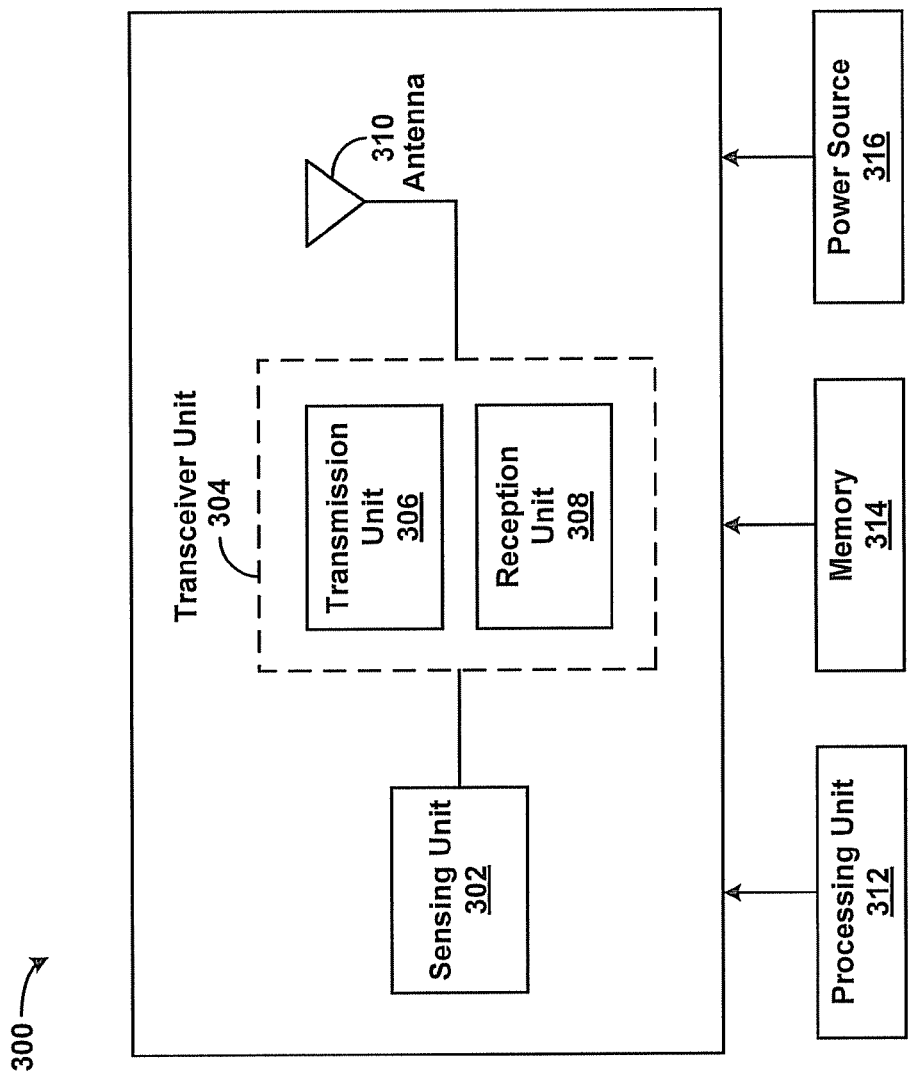
FIG. 3 is a block diagram illustrating an example sensor.

FIG. 3 is a block diagram illustrating an example sensor 300. The sensor 300 includes a sensing unit 302 coupled to a transceiver unit 304 that includes a transmission unit 306 and a reception unit 308. The transceiver unit 304 is coupled to an antenna 310.

The sensing unit 302 may be a hardware device that produces measurable responses to a change in a physical condition, such as temperature or pressure. The sensing unit 302 senses or measures physical data of an area to be monitored. The sensing unit 302 may be a passive sensing unit that senses data without manipulating the environment by active probing, and may or may not have a well-defined notion of direction of measurement. Alternatively, the sensing unit 302 may actively probe the environment, for example, using sonar, radar or seismic technology. The sensing unit 302 may measure or detect any kind of change in an area, and examples of types of sensing units include thermal sensors, electromagnetic sensors, pressure sensors, humidity sensors, vibration and shock sensors, chemical sensors including oxygen sensors and carbon monoxide detectors, light or photodetector sensors, infra-red sensors, radiation sensors including a Geiger counter, acoustic or sound sensors including microphones and seismometers, motion sensors, orientation sensors including gyroscopes, and distance or proximity sensors. Any combination of sensors may be used as well depending on a type of bio-event being monitored. One example commercially available sensor includes a portable radiation sensor referred to as iGem™ made by eV Products of Saxonburg, Pa. (USA). Many other commercially available sensors may be used as well.

The sensing unit 302 may output a continual analog signal that can be digitized by an analog-to-digital converter (not shown). The sensing unit 302 has a certain area of coverage for which the sensing unit 302 can reliably and accurately report a particular aspect that the sensing unit 302 is observing. For example, the sensing unit 302 may be able to detect occurrences over a circle having a 10 foot radius for some occurrences, or over a circle having a 1 mile radius for other occurrences. Although only one sensing unit 302 is shown, the sensor 300 may include multiple sensing units, and each sensing unit may or may not monitor or detect the same type of occurrences, for example.

The transceiver unit 304 may operate in four different modes: transmit, receive, idle, and sleep, for example. If the transceiver unit 304 is not transmitting or receiving, then the transceiver unit 304 may be placed in sleep mode to conserve power, or idle mode. The transceiver unit 304 may transmit and receive signals simultaneously using the transmission unit 306 and the reception unit 308.

As mentioned above, the sensor 300 may additionally include a processing unit 312 and memory 314. The processing unit 312 may process data and control functionality of components in the sensor 300. The processing unit 312 may be embodied as a processor that accesses memory 314 to execute software functions stored therein. One skilled in the art of computer systems design will understand that the example embodiments are not limited to any particular class or model of processor. The processors may operate according to an operating system, which may be any suitable commercially available embedded or disk-based operating system, or any proprietary operating system. Further, the processors may comprise one or more smaller central processing units, including, for example, a programmable digital signal processing engine or may also be implemented as a single application specific integrated circuit (ASIC) to improve speed and to economize space. In general, it should be understood that the processing unit 312 could include hardware objects developed using integrated circuit development technologies, or yet via some other methods, or the combination of hardware and software objects that could be ordered, parameterized, and connected in a software environment to implement different functions described herein. Also, the hardware objects could communicate using electrical signals, with states of the signals representing different data.

Furthermore, as mentioned, the processing unit 312 may include or have access to memory 314 that stores information such as previously transmitted or received signal strengths, for example. The memory may include random access memory (RAM), flash memory or long term storage, such as read only memory (ROM) or magnetic disks, for example.

The sensor 300 may also include or be coupled to a power source 316. The power source 316 may be an independent power source such as a battery or a solar power source, or the sensor 300 may be connected to other types of conventional power sources.

The processing unit 312 will receive measurements from the sensing unit 302 and evaluate the measurements. The measurements output by the sensing unit 302 will be an indication of a detection of an occurrence. The processing unit 312 may determine a level of confidence that the detection of the occurrence relates to an event being monitored. The processing unit 312 may do so by determining a magnitude of the measurement, or determining a number of measurements received over a specified amount of time, for example (and comparing actual measurements to baseline measurements to establish a confidence level). The processing unit 312 may then direct the sensor to transmit signals at a power level proportional to the level of confidence. Thus, the sensor 300 may sense or detect a change in a surrounding or nearby environment, and send a signal wirelessly using the transmission unit 306 and the antenna 310 to other sensors in the surrounding or nearby environment.

At the same time, the other sensors in the surrounding or nearby environment may sense or detect a physical change as well, and may also send a wireless signal to sensors in the area. In this manner, sensors within a geographical area may communicate with each other to inform each other of a detection. A compilation of sensor information can be used to construct a description of a possible source, magnitude, type, location or time of an event. For example, a time and magnitude can be estimated based on sensor measurements using signal processing techniques (e.g., time signal was received, and magnitude of received signal strength). However, an amount of information that may be determined can depend on the nature of the sensor information being accumulated.

The processing unit 312 may also perform a function of monitoring an area. For example, the sensor 300 will receive signals from other sensors via the reception unit 308. The processing unit 312 may store the received signals (or indications of the received signals) in the memory 314. The received signals are sent by other sensors in the area. Thus, based on a received signal strength, the processing unit 312 can generate a coverage area map indicating an area over which the signals are transmitted. In addition, signals may be transmitted with a sensor identification or location identifier, and thus the processing unit 312 may determine the identifier and generate a coverage area map of received signals based on the identifier. Thus, a sensor unit may include position information (or, equivalently, an identifier that can be mapped to a position using a stored database created at the time of installation of the sensors) in a signal transmission that may be received by the public system telephone network (PSTN). The PSTN can then aggregate and route such information to a real-time web page that displays which sensors are on a boundary of a coverage area on a real-time basis, and a map such as shown in FIG. 1 can be generated and displayed.

Figure 4:
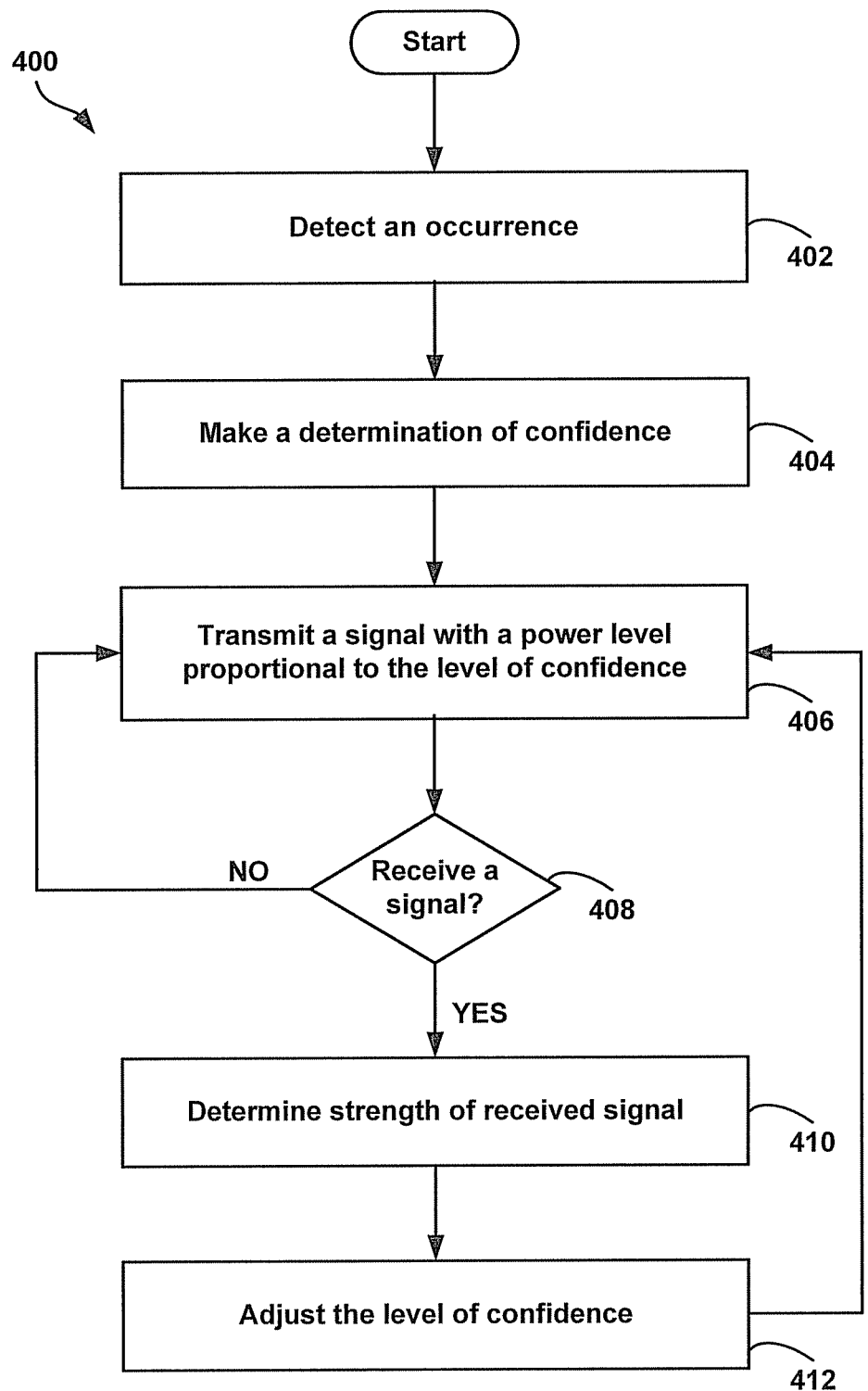
FIG. 4 is a flowchart depicting example steps of a method for scaling transmit power of sensors to indicate detection of an event.

FIG. 4 is a flowchart depicting example steps of a method for scaling transmit power of sensors to indicate detection of an event. It should be understood that the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. In addition, each block may represent circuitry that is wired to perform the specific logical functions in the process. Alternative implementations are included within the scope of the example embodiments of the present application in which functions may be executed out of order from that shown or discussed, including substantially concurrent or in reverse order, depending on the functionality involved, as would be understood by those reasonably skilled in the art.

Initially, as shown at block 402, a sensor will detect an occurrence. The occurrence may be defined as any noticeable change in a surrounding or nearby environment, or any difference in behavior of a monitored item in the surrounding or nearby environment. The occurrence will depend upon a particular event being monitored, and may include any type of event that can be monitored using any available sensor.

The sensor, or a processing unit coupled to the sensor, will then make a determination about a level of confidence of the detected occurrence correlating to an event being monitored, as shown at 404. For example, if this is a first occurrence that has been detected by the sensor over a specified amount of time, then a confidence level may be determined to be low that the event has occurred. However, if this is a fifth or sixth occurrence that has been detected by the sensor over a small amount of time, then a confidence level may be determined to be high that the event has or is occurring. Thus, the sensor and the processing unit may perform as a sequential detector by making measurements, accumulating the measurements over time, and as more and more measurements are accumulated, a threshold amount of measurements will eventually be accumulated that indicate that the event has or is occurring. A level of accumulation of measurements can be correlated to a level of confidence.

In addition, or alternatively to accumulating measurements, a level of confidence may be determined by identifying a strength of a signal indicating the detected occurrence. For example, if the sensor is detecting changes in temperature, and a sudden change of 20° C. is detected and measured, a sensing unit of the sensor will output a signal proportional to the 20 degree change. Similarly, if a 5° C. change in temperature is detected and measured, a sensing unit of the sensor will output a signal proportional to the 5 degree change. The sensing unit would output a signal of higher power due detecting to the 20 degree change than due to detecting the 5 degree change. Thus, a strength of the signal (e.g., voltage level of the signal) output by the sensing unit of the sensor can be correlated to a level of confidence as well.

If the sensor is part of a sensor node that includes multiple sensors, and all sensors are coupled to a central processing unit (such as shown in FIG. 2A), then each sensor may make a measurement of an occurrence and the processing unit will receive the measurements. The processing unit may then generate a single confidence level for the sensor node based on measurements received from all sensors in the node. In this manner, for example, if all sensors measure the occurrence, the processing unit may generate a high confidence level, but if only a portion of the sensors in the node measure the occurrence, the processing unit may generate a lower confidence level.

Next, as shown at block 406, the sensor will transmit a signal with a power level proportional to the level of confidence. Each sensor may wirelessly transmit or broadcast signals to other sensors that are positioned within a coverage area. The sensors do not necessarily transmit signals to a particular sensor, but rather, broadcast signals with a particular power level, and other sensors within a coverage area created by transmitting signals with the particular power level will receive the transmitted or broadcasted signals. In this manner, if the level of confidence is low, a signal will be transmitted with low power and may not be received by all other sensors in the coverage area. On the other hand, if the level of confidence is high, a signal will be transmitted with high power and could possibly be received by all other sensors in the coverage area, for example.

Subsequently, the sensor may or may not receive a signal from another sensor, as shown at block 408. If not, the sensor will continue to transmit signals with a power level proportional to the determined level of confidence, as shown at block 406.

If the sensor receives a signal from another sensor, then the sensor will determine a signal strength of the received signal, as shown at block 410. For example, the sensor may be located far away from the other sensor, and thus far away from the event detected by the other sensor, and may receive signal from the other sensor that is weak. Alternatively, if the sensor is located close in proximity to the other sensor, and thus close to the event detected by the other sensor, the sensor will receive a signal from the other sensor that is strong.

A signal strength refers to a magnitude of an electric field at a reference point that is a certain distance from a transmitting antenna. Spectral density or signal-to-noise ratio (SNR), $E_b/N_o$, where $E_b$ represents signal strength and $N_o$ represents noise in an air interface, may be used as a measurement of a level of signal strength. The SNR may be calculated by taking the ratio of an average power of a received signal over time versus an average power of received background noise over time.

Additionally, to measure signal strength, a sensor may receive and store signals over a given time and take an average power of the strength of the signals. The sensor may do so when positioned within an environment where fading is present that distorts signals due to multipath propagation, for example.

If a sensor experiences interference in a wireless communication channel, the interference may increase a power level of a received signal, which will lead the sensor to infer that the received signal has a high power level than originally intended (and thus, that the confidence level of the sensor that sent the signal will be determined to be higher than actual). A sensor may not receive messages constantly. Thus, during a period in which no signals are received, the sensor may measure ambient inference power levels, and subtract the inference power levels from any received signals to determine a power level of a received signal that corresponds to a power level of the signal. Removing interference can give a better approximation of a power level of a received signal, and of a confidence level of a sensor that sent the signal.

After determining a strength of the received signal, a level of confidence is adjusted accordingly, as shown at block 412, and subsequently a signal is transmitted with a power level proportional to the adjusted level of confidence, as shown at block 406. For example, referring to FIG. 1, the sensor node 106 will transmit a signal if the sensor node 106 detects an occurrence. If the sensor node 108 receives the transmitted signal from the sensor node 106, then the sensor node 108 is within a coverage area of the sensor node 106. Then, it will be determined that at least two sensors within a given coverage area have detected the occurrence, and thus, when the sensor node 108 receive the signal from the sensor node 106, it is a form of a check or validation of the sensor node's 108 measurements. Thus, the level of confidence at the sensor node 108 can be increased, such as by increasing the level by one unit (e.g., where a unit may be defined at 10%, 20%, etc.), and a signal will be transmitted with a higher power so as to be received by more sensors, for example.

Further, if the received signal strength is high, the confidence level may be adjusted more specifically. For example, if a received signal strength is high, it can be determined that the sensor that sent the signal is nearby, and thus, a bio-event is nearby as well. Alternatively, a high received signal power indicates that the sensor that sent the signal has a high level of confidence that the bio-event has or is occurring. The received signal power is proportional to the neighboring sensor's confidence level. As a result, the confidence level of the sensor who received the signal can be increased with a greater certainty that the bio-event has or is occurring near the sensor.

Figure 5A:
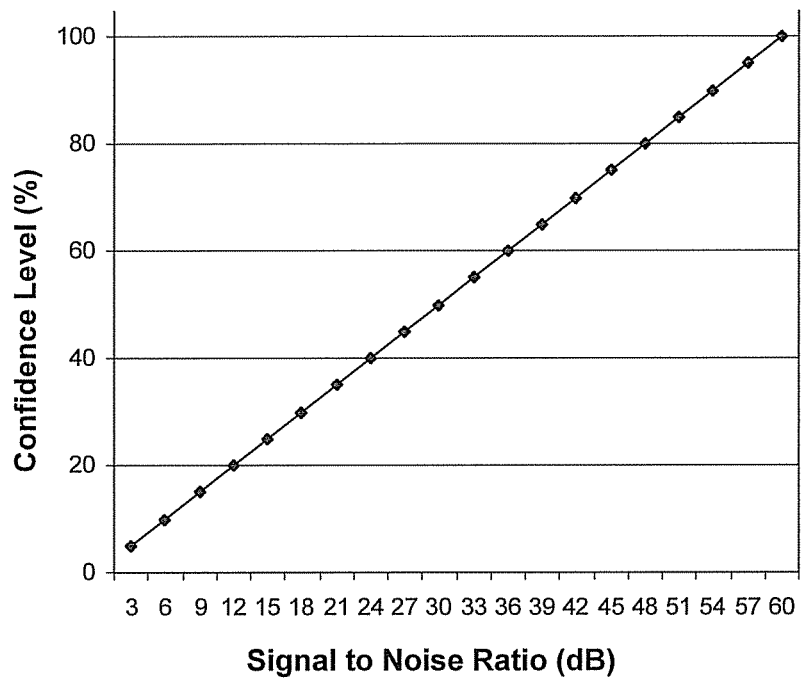
FIGS. 5A-5B illustrate example graphs detailing relationships between a confidence level and a received signal strength.
Figure 5B:
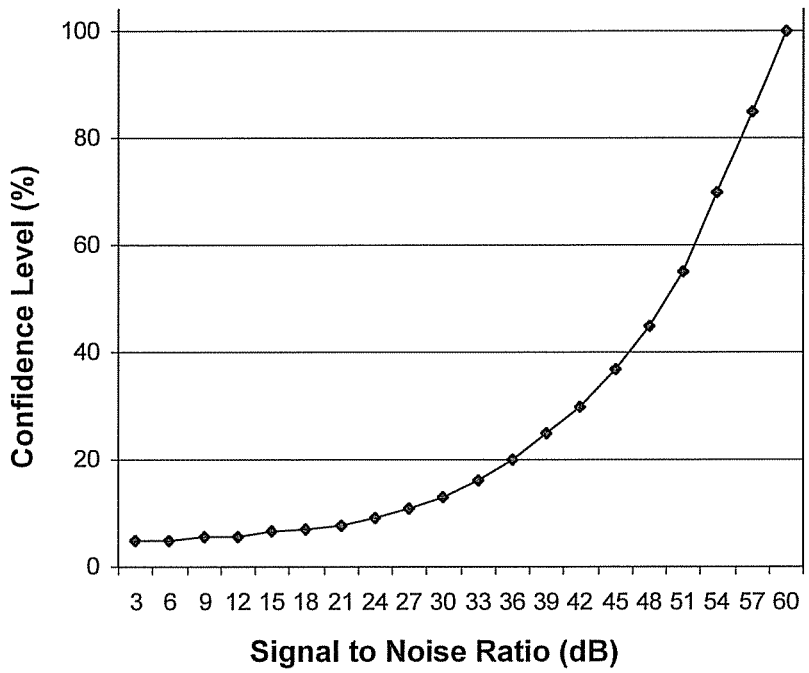

FIG. 5A illustrates an example graph detailing one relationship between a confidence level and a received signal strength. As shown, the confidence level may increase linearly as the received signal strength increases. FIG. 5B illustrates another example of a graph detailing another relationship between the confidence and the received signal strength. In FIG. 5B, the confidence level increases exponentially as the received signal strength increases. In this manner, it is determined that once the received signal strength reaches about 50 dB, then the sensor will increase a confidence level drastically. Other power levels may be chosen as a point at which the confidence level changes drastically. In addition, other relationships may be used between the confidence level and the received signal strength. Thus, the graphs shown in FIGS. 5A-5B are only two examples, and many more exist depending on the nature of the event being monitored.

In addition, a sensor may adjust a level of confidence based on a number of received signals. For example, if the sensor only receives one signal, then only one other sensor in the area has detected an occurrence. The sensor that received the signal may then adjust a confidence level by a small amount. However, if a sensor receives many other signals (e.g., 15-20), then that indicates that many other sensors in the area have also detected an occurrence, which increases the likelihood that the occurrence has or is occurring. Thus, the sensor that received the many other signals can increase a confidence level by a larger amount.

As another example, a sensor may adjust a level of confidence based on how frequently the sensor receives signals. For example, the confidence level may be increased slight if the sensor receives one signal per minute, but the confidence level may be increased by a large amount if the sensor receives one signal per second. The level of confidence may be adjusted in many other ways based on signals received from other sensors depending on the type of event being monitored.

Still further, upon receiving a signal, a sensor may determine a level of correlation between the received signal and its own detection. For example, for a radiation event, depending on a position of two sensors, each may measure different levels of radiation, and thus, will have different levels of confidence. When the two sensors are deployed, the sensors may be calibrated or tested to determine a correlation between the sensors. To calibrate a sensor, for example, a sensor X can calibrate a correlation of measurements with those of a neighboring sensor Y by correlating a confidence level of sensor X with estimates of confidence levels from sensor Y. As mentioned above, sensor X can determine sensor Y's confidence level by measuring a received signal strength of a signal received from sensor Y. A high signal strength power would indicate that sensor Y is relatively more confident of a presence of an occurrence as compared to sensor X, and a low signal strength power would indicate that sensor Y is less confident of a presence of an occurrence as compared to sensor X. This data may be stored at each sensor, and used by the sensor to adjust a level of confidence.

Alternatively, as mentioned above, a correlation factor may be determined based on a number of signals received from neighboring sensors, or based on a number of signals received from neighboring sensors that have a signal strength of a given level, for example.

The sensor may transmit signals with any desired regularity, such as once a minute as long as the occurrence is still being detected or only every time an occurrence is detected. Alternatively, the sensor may adjust the regularity with which signals are transmitted based on the level of confidence of the detection. For example, if the level of confidence is high, the sensor may transmit signals in a repetitive fashion and more quickly (e.g., once every 5 seconds) than if the confidence level is low (e.g., once every minute). If the level of confidence is high, the sensor may also broadcast signals in all directions, for example. And if the confidence is low, the sensor may broadcast signals in a directional manner, such as only to highly populated areas for example.

The sensor may continue to transmit signals until the occurrence is no longer detected, or until the level of confidence falls below a threshold, e.g., such as below 30% confident.

Figure 6:
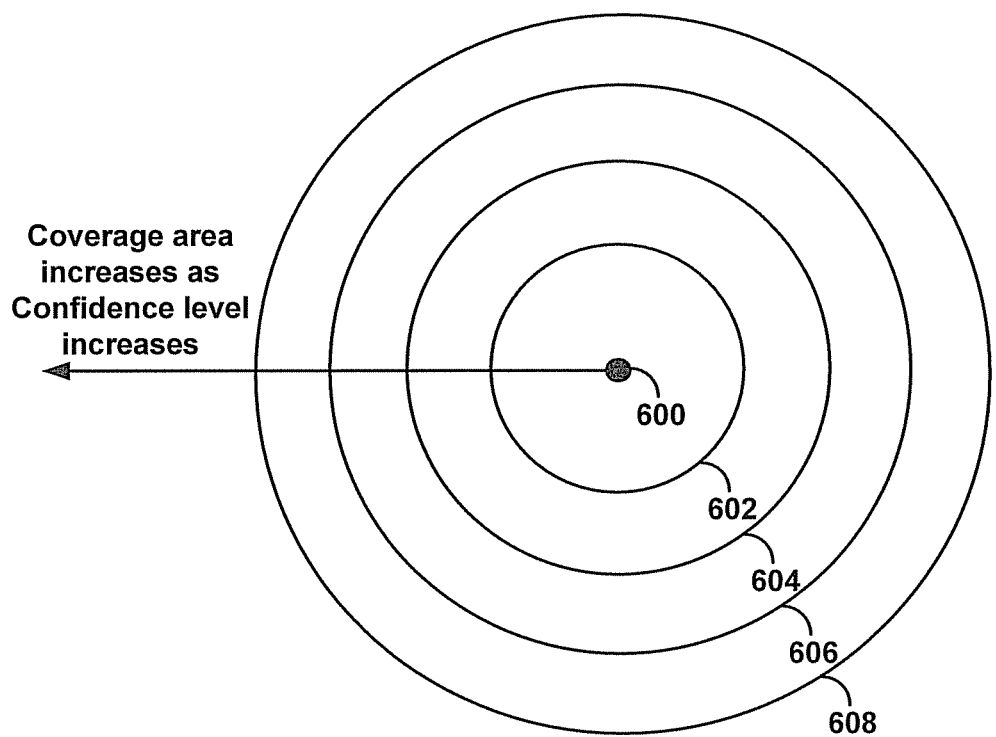
FIG. 6 is a diagram illustrating an example conceptual coverage area of a sensor.

FIG. 6 is a diagram illustrating a conceptual coverage area of a sensor 600. A coverage area of the sensor 600 is a geographic area over which the sensor 600 can communicate. Coverage depends on several factors, such as technology and radio frequency, for example. Some frequencies provide better regional coverage, while other frequencies penetrate better through obstacles, such as buildings in cities. The coverage area of the sensor 600 depends on strength of signals transmitted from the sensor. Signal strength may be boosted by high power transmissions or more effective antennae, for example. Still further, signal strength may be boosted by high power amplifiers. Several commercially available directional antennas may be employed for different carrier frequencies. Such antennas are the high gain (i.e., effective) antennas, and include, for example, the Cisco Aironet High Gain Omnidirectional Antenna available from Cisco Systems, Inc. of San Jose, Calif. (USA) and other various antennas sold by RadioLabs of Fortuna, Calif. (USA).

The sensor 600 may transmit signals over a coverage area 602 based on a low confidence level of a detected occurrence, such as about 35%. If the confidence level of a detected occurrence rises, then the sensor may increase a signal transmission power level to transmit signals over a larger coverage area, such as coverage area 504 for confidence levels as high as about 50%, for example. If the confidence level of a detected occurrence continues to rise, or is determined to be at a high level, the sensor 600 may transmit signals over coverage area 604, 606, or 608, for example. Coverage area 608 may indicate a largest geographic area to which the sensor 600 can transmit signals, and thus, may also indicate an area to which the sensor 600 will transmit signals if a highest level of confidence is achieved.

Figure 7A:
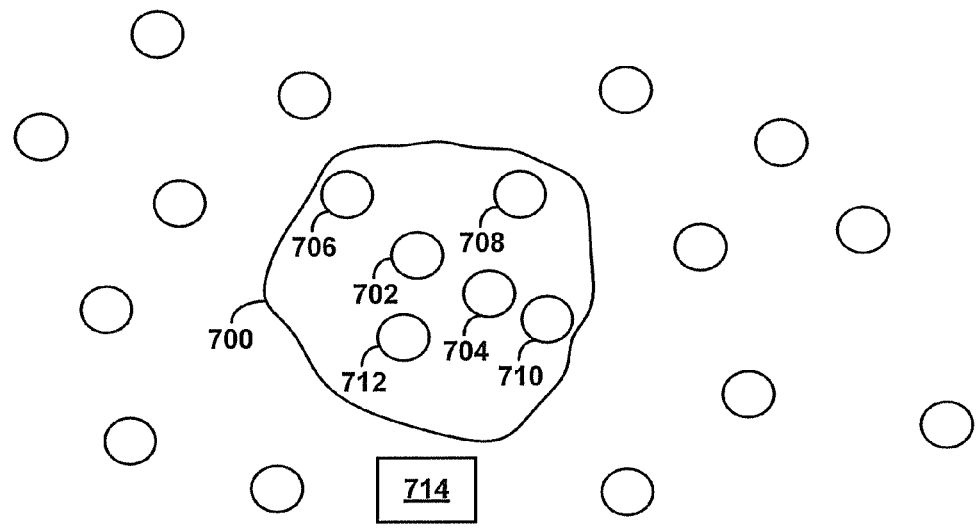
FIGS. 7A-7B illustrate example conceptual allocations of sensors throughout a geographic area.

FIG. 7A illustrates a conceptual allocation of sensors throughout a geographic area. An event or occurrence is depicted by 700. Sensors 702, 704, 706, 708, 710 and 712 are all geographically located within an area of the event 700 and each detects the event 700 to a certain level. Sensors 702 and 704 are located at a center of the event, and may detect strongest levels of the event, such as a largest temperature change, a highest amount of radiation, etc. Sensors 702 and 704 will then transmit signals that have a power level proportional to the level of confidence of the event, and thus, will be transmitted over a given coverage area.

Sensors 706, 708, 710 and 712 may be within the given coverage area and may receive the signals transmitted from the sensors 702 and 704. However, because the sensors 706, 708, 710 and 712 are not located at the center of the event, those sensors will not detect the event as strongly as the sensors 702 and 704. Thus, even though sensors 706, 708, 710 and 712 receive signals from sensors 702 and 704 indicating the event, the sensors 706, 708, 710 and 712 will transmit signals of a low power due to a low detection of the event (and thus, lower confidence level). As a result, the sensors 706, 708, 710 and 712 will transmit signals over a small coverage area, and fewer sensors within the geographic area will receive the signal.

A sensor that transmits signals at a predetermined power level may be designated as being located at a boundary region of the event region. If a sensor transmits signals at about 50% power, for example, then the sensor may be considered to be at a boundary region of the event region. In FIG. 7A, sensors 706, 708, 710 and 712 may transmit signals at a boundary region level, and may indicate a boundary of the event region. Other signal transmission power levels may also be used to identify a boundary region depending on the type of event being monitored.

Monitoring units, such as monitoring unit 714, may be positioned throughout a geographic area and may receive signals from all sensors 702, 704, 706, 708, 710 and 712. The monitoring unit 714 can then determine boundary regions, for example, using received signal power levels. In addition, a sensor identifier or location identifier may be embedded in the signals, and the monitoring unit 714 can use the identifier information to determine from which sensors signals have been received and to determine boundary regions of a detected event, for example.

Figure 7B:
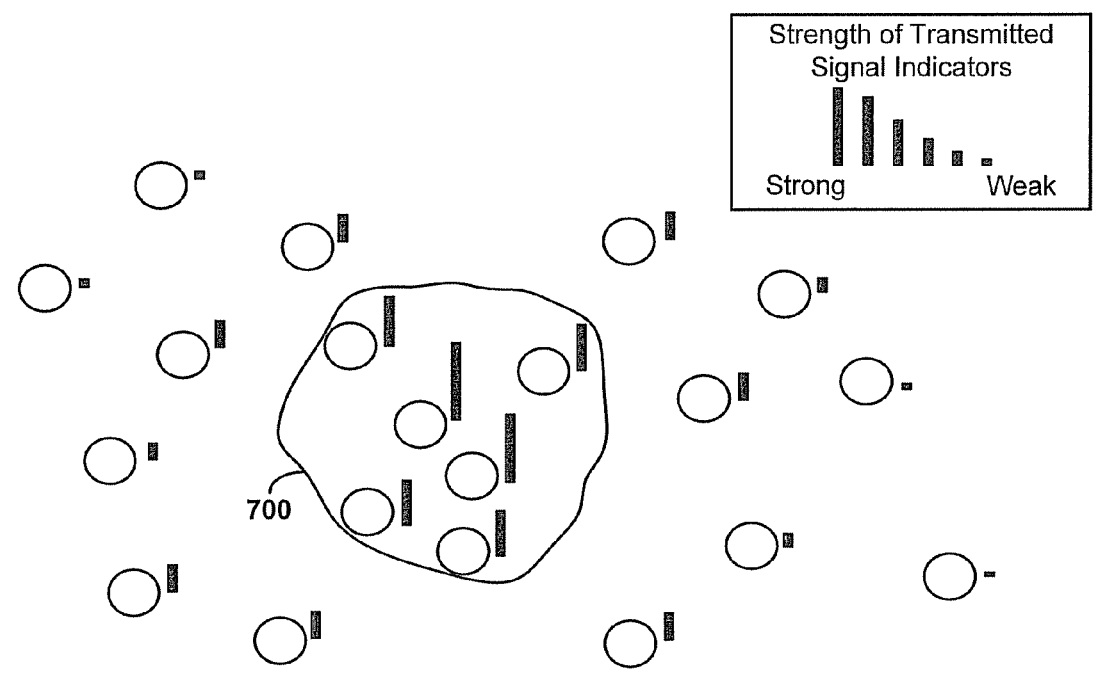

FIG. 7B illustrates another example of the conceptual allocation of sensors throughout a geographic area. In FIG. 7B, the same event 700 is presumed to have occurred, and sensors within an area of the event 700 will detect the event and transmit signals that have a power level proportional to a confidence level of the sensors. FIG. 7B illustrates a strength of transmitted signals per sensor using a signal bar. A height of a signal bar indicates a transmit power level (which is proportional to the confidence level of a sensor about the occurrence of the event). A sensor that detects the event more heavily (and has a higher level of confidence) will transmit a signal with a higher power level than a sensor outside of the event region and that may only subtlety detect the event. As shown, all sensors within the event area 700 transmit signals at higher power levels than sensors located outside of the event area 700.

Thus, instead of communicating a decision about whether an event has occurred, a sensor scales a signal transmission power level in a manner that is proportional to a confidence level of a decision about the event. This enables a fast, distributed, wireless mechanism to improve accuracy of biosensor nodes in a geographically distributed biosensor network. The sensor nodes no longer have to determine which nodes to transmit signals. Nodes that detect the event automatically begin performing as long range beacons that warn about the occurrence of the event since these sensor nodes transmit at a higher transmit power. This improves dissemination of information about events such as bioterrorism, spread of infectious diseases, etc.

Sensors or sensor nodes may be positioned closely to each other, or farther apart so as to establish a more broad detection area. A smaller distance between sensors gives a higher resolution of detection. For example, if sensors are located close enough to each other so that the sensors can receive signals from a large number of nearby or neighboring sensors, then the sensors will be able to determine a better level of confidence. To determine placement of sensors, it may be that a sensor is placed as far from another sensor as possible while still being able to receive a signal from the other sensor, or while still being able to receive a signal from the other sensor that has a signal strength of a given level.

A sensor's distance between a neighboring sensor may cause the sensor to receive a signal that has a very low power (due to loss of power within the wireless channel). In this instance, the sensor will correctly use the received signal power as an indicator of proximity to the event detected by the neighboring sensor, and because the received signal power is low, the sensor will determine that the event is not far enough so that the sensor probably does not detect the event and probably will not transmit a signal. However, if fading or interference within a wireless channel cause a sensor to receive a signal that has a low power level, the sensor will not be able to accurately infer the neighboring sensor's confidence level from the received signal power. In this instance, sensors may also embed a message in a transmitted signal to convey additional information. For example, a level of confidence may be embedded in a transmitted signal using four bits of information to obtain 16 levels of confidence. Thus, as long as a sensor can receive and decode a signal, the sensor can determine a neighboring sensor's level of confidence no matter the level of interference in the channel.

Figure 8:
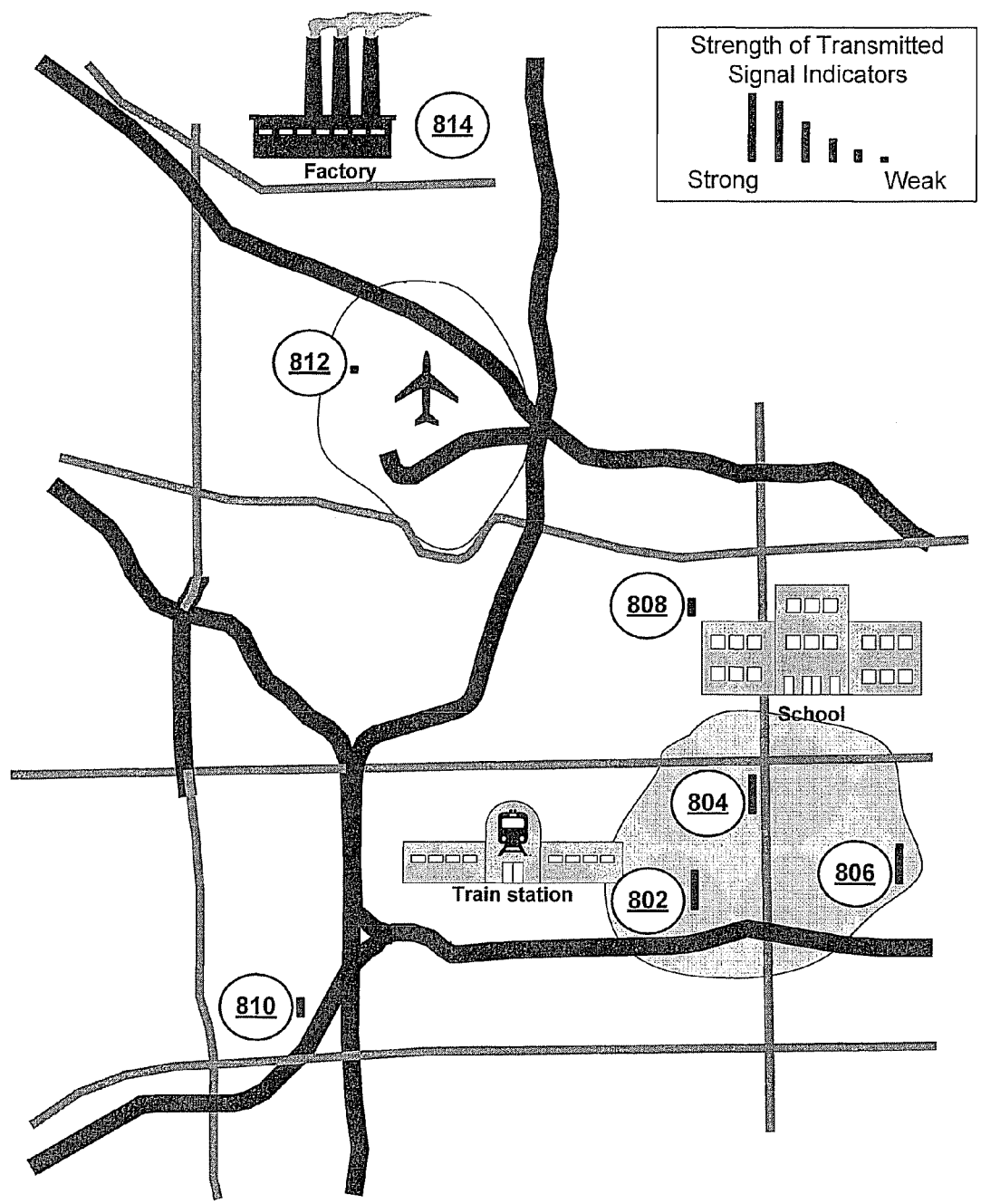
FIG. 8 illustrates another example conceptual geographical area and placement of example sensor nodes within the geographical area.

FIG. 8 illustrates another conceptual geographical area and placement of example sensor nodes 802, 804, 806, 808, 810, 812 and 814 within the geographical area. A bio-event may occur in a given area, and sensor nodes 802, 804 and 806 may be within the given area and may detect the bio-event. Each of sensors 802, 804 and 806 will transmit signals that have a power level proportional to a confidence level of the sensors. Additionally, each sensor 802, 804 and 806 may be within a coverage area of each other, and thus, may receive signals from each other. In turn, each sensor 802, 804 and 806 may raise a confidence level of its determination and will transmit signals at a higher power level. Subsequently, sensors located farther away from sensors 802, 804 and 806 may receive signals from the sensors 802, 804 and 806. Because other sensors, such as sensors 808, 810, 812 and 814 are located far away from sensors 802, 804 and 806, the sensors 808, 810, 812 and 814 may receive a signal that has a low power level from the sensors 802, 804 and 806. Each of sensors 808, 810, 812 and 814 may then begin transmitting signals proportional to a confidence level, which will be low because the sensors 808, 810, 812 and 814 may not themselves detect the bio-event. Sensor 814, for example, may receive a signal from sensors 802, 804 and 806 that is so weak that sensor 814 will not even begin transmitting signals.

In the example shown in FIG. 8, sensors 802, 804 and 806 may be considered to mark a boundary of the bio-event. The present application enables a natural distributed way of locally detecting a boundary of an event region. A demarcation of the boundary region enables the boundary sensor nodes to notify the public to avoid the event region. For example, vehicles traveling through the area may transmissions from the boundary sensor nodes and may reroute themselves to avoid the event region. Thus, the sensor nodes may transmit signals using an AM/FM frequency that can be received by car radios, for example. Alternatively, a central signal transmission unit may receive signals from the sensors, and upon receiving a sufficient number of signals, or signals that have a sufficient power level, the central signal transmission unit may begin broadcasting warning signals using an AM/FM frequency to warn the public.

In addition, or alternatively to broadcasting warning signals, the sensors or a central signal transmission unit may be coupled to the public switched telephone network (PSTN), and warning signals or messages can be routed using the PSTN. Further, as mentioned above, the PSTN may aggregate information received from sensors and route such information to a real-time web page database system that displays which sensors are on a boundary of a coverage area on a real-time basis, and a map such as shown in FIG. 7A-7B or FIG. 8 can be generated and displayed.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

It should be further understood that this and other arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

What is claimed is:
1. A method, comprising:
receiving, by a processor unit and from a first sensor unit, a first signal indicative of an occurrence of an event;
determining, by the processor unit, a level of confidence that the event occurred based on the first signal;
receiving, by the processor unit and from a second sensor unit, a second signal indicative of the occurrence of the event;
adjusting, by the processor unit, the level of confidence based on a signal strength of the second signal from the second sensor unit;

establishing, by the processor unit, a signal transmit power level for a third signal, from the first sensor unit, that corresponds to the adjusted level of confidence; and causing, by the processor unit, the first sensor unit to transmit the third signal from the first sensor unit to a neighbor sensor unit at the established signal transmit power level, thereby enabling the first sensor unit to perform as a beacon and communicate the occurrence of the event as a warning to one of a user or a vehicle located in a boundary region of the occurred event.

2. The method of claim 1, wherein receiving, by the processor unit, the first signal comprises receiving measurements from the first sensor unit, and wherein determining the level of confidence that the event occurred comprises determining a quantity of the measurements received, from the first sensor unit, that indicate the occurrence of the event.

3. The method of claim 1, wherein determining the level of confidence that the event occurred comprises determining a magnitude of a measurement received from at least one of the first sensor unit and the second sensor unit.

4. The method of claim 3, wherein determining the level of confidence comprises establishing the level of confidence to be proportional to the magnitude of the measurement.

5. The method of claim 4, wherein the level of confidence and the magnitude of the measurement have a linear relationship.

6. The method of claim 4, wherein the level of confidence and the magnitude of the measurement have an exponential relationship.

7. The method of claim 1, further comprising:
receiving multiple signals from multiple sensor units, wherein each signal of the multiple signals indicates at least one of a plurality of occurrences; and
making a single determination about a level of confidence that the plurality of occurrences relates to the event.

8. The method of claim 1, wherein a signal strength of the third signal, from the first sensor unit, is proportional to the established signal transmit power level.

9. The method of claim 1, further comprising:
receiving a plurality of signals, from other sensor units, indicative of the occurrence of the event; and
adjusting the level of confidence based on a quantity of the plurality of signals.

10. The method of claim 1, further comprising:
determining a level of correlation between the second signal from the second sensor unit and a measurement by the first sensor unit; and
adjusting the level of confidence based on the level of correlation between the second signal from the second sensor unit and the measurement by the first sensor unit.

11. The method of claim 10, wherein the first signal indicates the measurement by the first sensor unit.

12. The method of claim 10, further comprising establishing a signal transmit frequency level of the first sensor unit that is proportional to the adjusted level of confidence, wherein the signal transmit frequency level indicates a frequency of transmission of signals of the first sensor unit.

13. The method of claim 1, further comprising:
receiving signals transmitted from other sensor units;
determining a signal strength of the signals transmitted from the other sensor units; and
determining the boundary region of the event based on the signal strength of the signals transmitted from the other sensor units, wherein the boundary region of the event includes a geographical area in which occurrences related to the event are detected by sensor units within the geographical area.

14. The method of claim 13, further comprising establishing a two-dimensional map indicative of the boundary region of the event.

15. A system, comprising:
a first sensor unit configured to generate a first signal indicative of an occurrence of an event;
a transceiver configured to receive, from a second sensor unit, a second signal indicative of the occurrence of the event; and
a processor unit coupled to the first sensor unit and the transceiver, and configured to:
receive the first signal from the first sensor unit;
determine a strength of the first signal, wherein the strength of the first signal is indicative of a boundary region of the occurred event;
determine a level of confidence that the event occurred based on the strength of the first signal;
determine a strength of the second signal, wherein the strength of the second signal is indicative of the boundary region of the occurred event;
adjust the level of confidence based on the strength of the second signal from the second sensor unit;
establish a signal transmit power level for a third signal, from the first sensor unit, that corresponds to the adjusted level of confidence; and
cause the first sensor unit to transmit the third signal, from the first sensor unit to a neighbor sensor unit, at the established signal transmit power level, thereby to enable the first sensor unit to perform as a beacon and communicate the occurrence of the event as a warning to one of a user or a vehicle located in the boundary region of the occurred event.

16. The system of claim 15, wherein:
the processor unit is configured to receive measurements from the first sensor unit, and
to determine the level of confidence that the event occurred, the processor unit is configured to determine a quantity of the measurements received, from the first sensor unit, that indicate the occurrence of the event.

17. The system of claim 15, wherein to determine the level of confidence that the event occurred, the processor unit is configured to determine a magnitude of a measurement received from at least one of the first sensor unit and the second sensor unit.

18. A non-transitory computer-readable medium that stores executable instructions that, in response to execution, cause one or more processors to perform or control performance of operations to:
detect, from a first sensor unit, a first signal indicative of an occurrence of an event;
determine a level of confidence that the event occurred based on the first signal;
detect, from a second sensor unit, a second signal indicative of the occurrence of the event;
adjust the level of confidence based on a signal strength of the second signal from the second sensor unit;
establish a signal transmit power level for a third signal, from the first sensor unit, that corresponds to the adjusted level of confidence; and
cause the first sensor unit to transmit the third signal, from the first sensor unit to a neighbor sensor unit, at the established signal transmit power level, thereby to enable the first sensor unit to perform as a beacon and communicate the occurrence of the event as a warning to one of a user or a vehicle located in a boundary region of the occurred event.

19. The non-transitory computer-readable medium of claim 18, wherein the executable instructions comprise instructions that, in response to execution, cause the one or more processors to perform or control performance of at least one operation to:
- obtain, by the one or more processors, measurements from the first sensor unit,
- wherein a quantity of the measurements received, from the first sensor unit, that indicate the occurrence of the event is used to determine the level of confidence that the event occurred.

20. The non-transitory computer-readable medium of claim 18, wherein a magnitude of a measurement received, from at least one of the first sensor unit and the second sensor unit, is used to determine the level of confidence that the event occurred.

* * * * *